(12) United States Patent
Huster et al.

(10) Patent No.: US 11,324,512 B2
(45) Date of Patent: May 10, 2022

(54) MAGNETIC SPHINCTER AUGMENTATION DEVICE FOR URINARY INCONTINENCE

(71) Applicant: Torax Medical, Inc., Shoreview, MN (US)

(72) Inventors: Celeste L. Huster, Blaine, MN (US); Brandon D. Bullitt, Indianapolis, IN (US); Kyle P. Taylor, Greenfield, MN (US); Jerome K. Grudem, Jr., Rogers, MN (US); Janet L. DeMarchi, Minnetonka, MN (US)

(73) Assignee: Torax Medical, Inc., Shoreview, MN (US)

( * ) Notice: Subject to any disclaimer, the term of this patent is extended or adjusted under 35 U.S.C. 154(b) by 609 days.

(21) Appl. No.: 16/171,712

(22) Filed: Oct. 26, 2018

(65) Prior Publication Data
US 2020/0129184 A1    Apr. 30, 2020

(51) Int. Cl.
*A61B 17/12*    (2006.01)
*A61F 2/00*    (2006.01)
*A61B 17/00*    (2006.01)

(52) U.S. Cl.
CPC .. *A61B 17/12099* (2013.01); *A61B 17/12131* (2013.01); *A61F 2/0036* (2013.01);
(Continued)

(58) Field of Classification Search
CPC ...... A61B 17/12–12013; A61B 17/122; A61B 17/1227; A61B 2017/00805;
(Continued)

(56) References Cited

U.S. PATENT DOCUMENTS 2,129,494 A * 9/1938 Dinhofer .................. A44C 5/16
                                                          24/265 R
5,122,136 A   6/1992 Guglielmi et al.
(Continued)

FOREIGN PATENT DOCUMENTS

CN     108294844 A  *  7/2018  ........... A61F 2/0036
DE        3011742 A1    10/1981
(Continued)

OTHER PUBLICATIONS

Machine translation of CN 108294844A retrieved from EPO (espacenet.com) on Feb. 19, 2021 (Year: 2018).*
(Continued)

*Primary Examiner* — Catherine B Kuhlman
(74) *Attorney, Agent, or Firm* — Frost Brown Todd LLC (57) ABSTRACT

A sphincter augmentation device includes a plurality of bodies and a flexible band coupled with the bodies. The bodies define a first circumferential portion of the device and are magnetically biased toward one another. The flexible band defines a second circumferential portion of the device such that the bodies are arranged non-axisymmetrically about a central axis of the device. The device is sized to be positioned around a human urethra so that the bodies and the flexible band bear inwardly against the urethra. The device is configured to transition between a radially expanded state and a radially contracted state by the magnetic bias of the bodies to constrict the urethra.

20 Claims, 8 Drawing Sheets

(52) U.S. Cl.
CPC ............ *A61B 2017/00805* (2013.01); *A61B 2017/00876* (2013.01); *A61F 2210/009* (2013.01)

(58) Field of Classification Search
CPC ........... A61B 2017/00818; A61B 2017/00827; A61B 2017/00876; A61B 2017/12004–12018; A61F 2/0004; A61F 2/0031–0036; A61F 2/004; A61F 2/0054; A61F 6/20–206; A61F 2210/009; A61F 5/005–0066; A44C 5/00–246; A44C 9/00–02; A44C 5/16; A44C 5/185; A44C 5/2057; A44C 5/2066; A44C 5/2076; A44C 5/2085; A44C 9/0038; A41F 1/002; A44D 2203/00

See application file for complete search history.

(56) References Cited

U.S. PATENT DOCUMENTS

| | | | |
|---|---|---|---|
| 5,204,382 A | 4/1993 | Wallace et al. | |
| 5,509,888 A | 4/1996 | Miller | |
| 5,702,361 A | 12/1997 | Evans, II et al. | |
| 5,913,872 A * | 6/1999 | Suh | A61N 2/06 606/201 |
| 6,543,456 B1 | 4/2003 | Freeman | |
| 7,073,232 B1 * | 7/2006 | Fuhrman | A44C 5/2042 24/303 |
| 7,175,589 B2 | 2/2007 | Deem et al. | |
| 7,445,010 B2 | 11/2008 | Kugler et al. | |
| 7,695,427 B2 | 4/2010 | Kugler et al. | |
| 8,070,670 B2 | 12/2011 | Deem et al. | |
| 8,591,396 B2 | 11/2013 | Zemlok et al. | |
| 8,603,023 B2 | 12/2013 | Albrecht et al. | |
| 8,617,049 B2 | 12/2013 | Dlugos, Jr. et al. | |
| 8,636,751 B2 | 1/2014 | Albrecht et al. | |
| 8,715,157 B2 | 5/2014 | Berg et al. | |
| 8,734,475 B2 | 5/2014 | Ekvall et al. | |
| 8,870,742 B2 | 10/2014 | Dlugos, Jr. et al. | |
| 8,876,761 B2 | 11/2014 | Albrecht et al. | |
| 10,245,133 B2 | 4/2019 | Alharmi et al. | |
| 2002/0028980 A1* | 3/2002 | Thierfelder | A61B 17/06109 600/37 |
| 2005/0283235 A1* | 12/2005 | Kugler | A61F 5/0069 623/14.13 |
| 2009/0062824 A1* | 3/2009 | Berg | A61F 5/005 606/157 |
| 2011/0098731 A1* | 4/2011 | Whitbrook | A61F 2/0018 606/151 |
| 2015/0051443 A1* | 2/2015 | Kassab | A61F 5/005 600/37 |
| 2016/0058594 A1* | 3/2016 | Armenteros | A61F 5/0089 600/37 |
| 2019/0029689 A1* | 1/2019 | Shelton, IV | A61F 2/04 |
| 2020/0078158 A1* | 3/2020 | Popescu | A61F 2/02 |

FOREIGN PATENT DOCUMENTS

| | | |
|---|---|---|
| WO | WO 1993/015721 A1 | 8/1993 |
| WO | WO 1993/016658 A1 | 9/1993 |
| WO | WO 1993/019702 A1 | 10/1993 |
| WO | WO 1997/033632 A2 | 9/1997 |
| WO | WO 1998/044965 A1 | 10/1998 |
| WO | WO 2000/054835 A1 | 9/2000 |
| WO | WO 2001/047431 A2 | 4/2001 |
| WO | WO 2009/029228 A2 | 3/2009 |
| WO | WO 2018/001192 A1 | 1/2018 |

OTHER PUBLICATIONS

U.S. Appl. No. 15/914,381, entitled "Tunable Magnetic Sphincter Augmentation Device," filed Mar. 7, 2018.

International Search Report and Written Opinion dated Jan. 31, 2020 for Application No. PCT/IB2019/059193, 14 pgs.

* cited by examiner

MAGNETIC SPHINCTER AUGMENTATION DEVICE FOR URINARY INCONTINENCE

BACKGROUND

In some instances, it may be desirable to place a medical implant within or surrounding a biological lumen/passageway in order to improve or assist the function of, or otherwise affect, the biological lumen/passageway. Examples of such biological lumens/passageways include, but are not limited to, the esophagus, a fallopian tube, a urethra, or a blood vessel. Some biological passages normally function by expanding and contracting actively or passively to regulate the flow of solids, liquids, gasses, or a combination thereof. The ability of a biological passage to expand and contract may be compromised by defects or disease. One merely illustrative example of a condition associated with decreased functionality of a body passage is Gastro Esophageal Reflux Disease ("GERD"), which affects the esophagus.

Examples of devices and methods that have been developed to treat anatomical lumens by providing sphincter augmentation are described in U.S. Pat. No. 7,175,589, entitled "Methods and Devices for Luminal and Sphincter Augmentation," issued Feb. 13, 2007, the disclosure of which is incorporated by reference herein; U.S. Pat. No. 7,695,427, entitled "Methods and Apparatus for Treating Body Tissue Sphincters and the Like," issued Apr. 13, 2010, the disclosure of which is incorporated by reference herein; U.S. Pat. No. 8,070,670, entitled "Methods and Devices for Luminal and Sphincter Augmentation," issued Dec. 6, 2011, the disclosure of which is incorporated by reference herein; and U.S. Pat. No. 8,734,475, entitled "Medical Implant with Floating Magnets," issued May 27, 2014, the disclosure of which is incorporated by reference herein.

While various kinds and types of instruments have been made and used to treat or otherwise engage anatomical lumens, it is believed that no one prior to the inventors has made or used an invention as described herein.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Exemplary Urinary Sphincter Augmentation Devices

Figure 1:
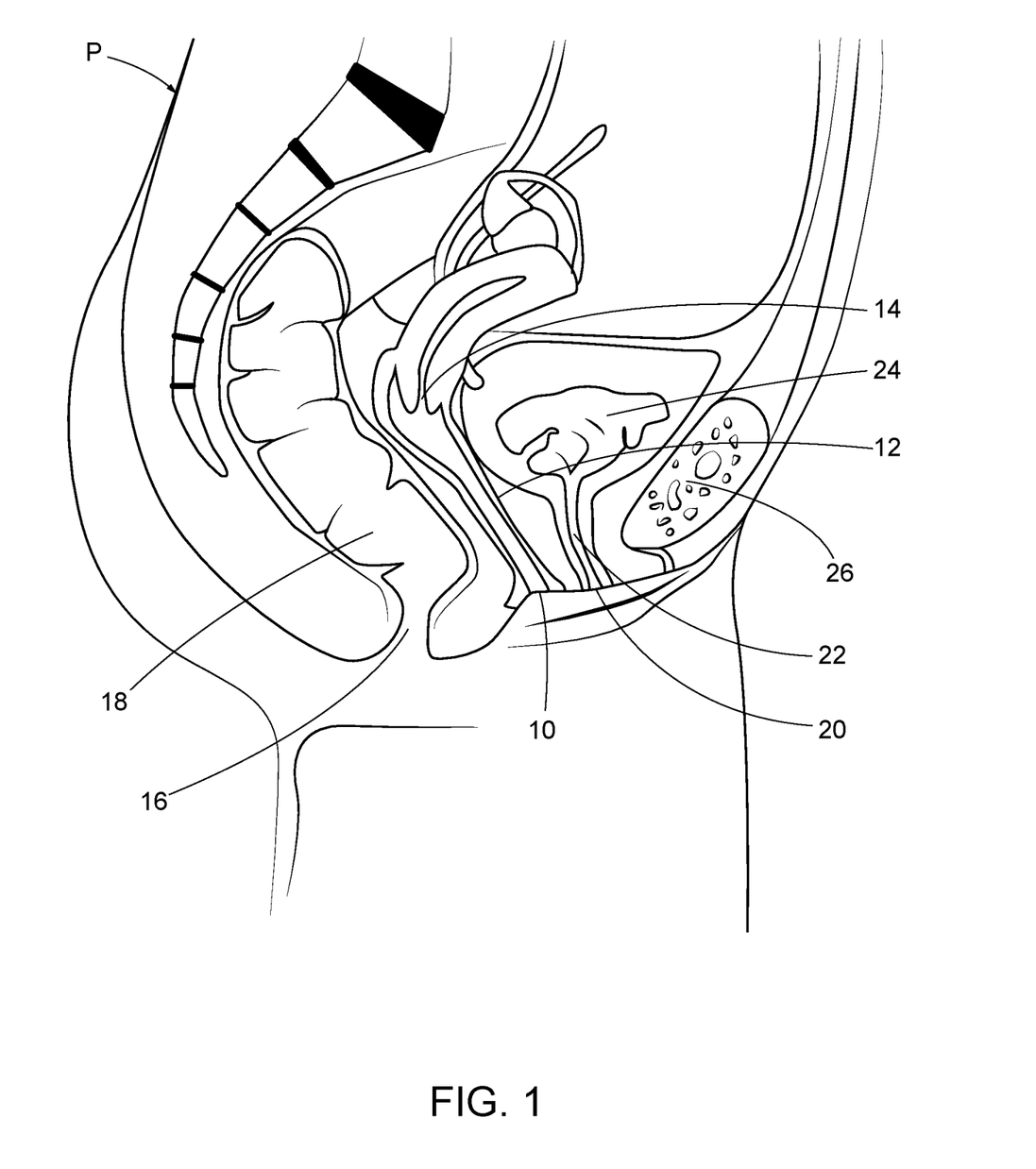
FIG. 1 depicts a cross-sectional side view of a female patient, taken along the sagittal plane, showing internal biological passages.
Figure 2:
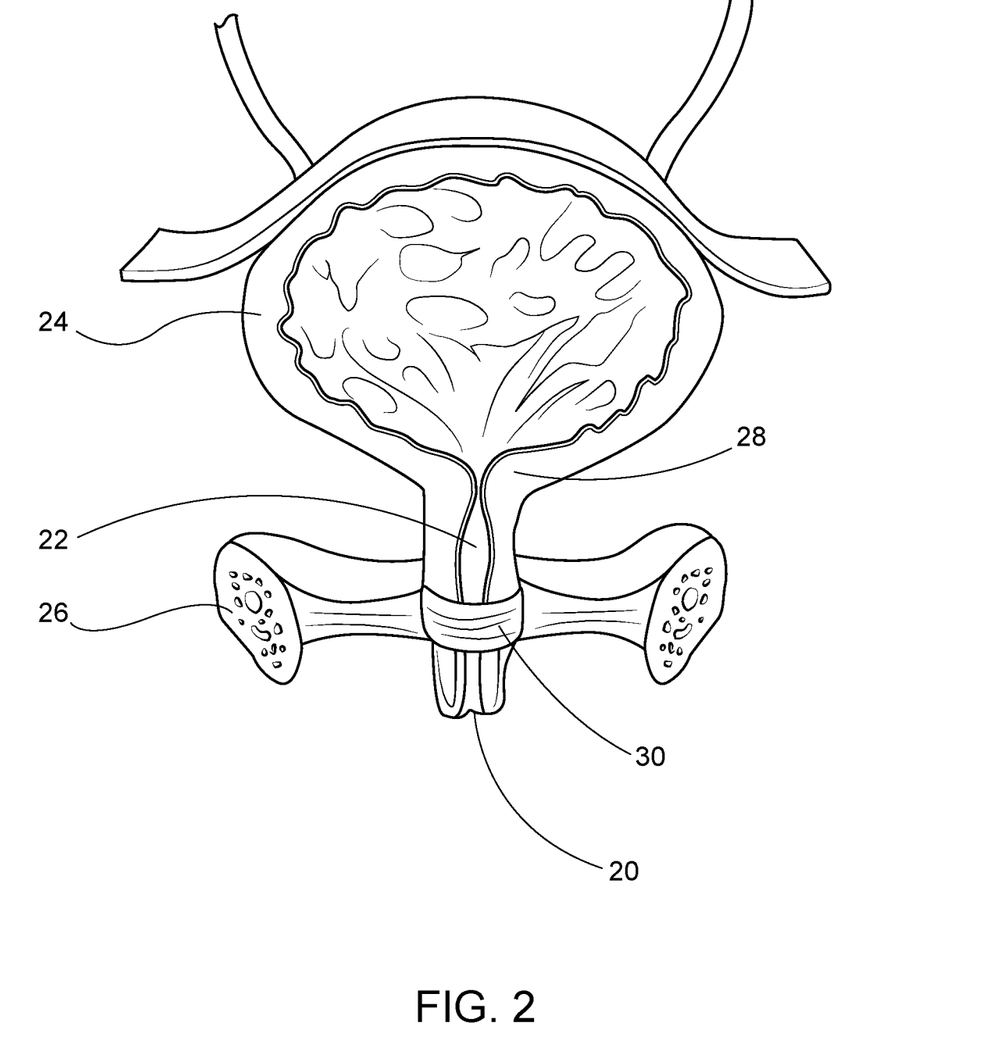
FIG. 2 depicts a cross-sectional front view of a female patient, taken along the coronal plane, showing the components of the patient's urinary system including the urethra and urethral sphincters.

FIG. 1 show selected anatomical features of a female human patient (P), including a vaginal opening (10) and a vaginal wall (12) that extends toward a cervix (14). Posterior of the vaginal opening (10), an anus (16) opens to a rectum (18). Anterior of the vaginal opening (10), an external urethral orifice (20) opens to a urethra (22), which communicates with a urinary bladder (24) positioned posterior of a pubic bone (26). As shown in FIG. 2, female patient (P) has an internal urethral sphincter (28) positioned at a superior end of the urethra (22), and an external urethral sphincter (30) positioned inferior of internal urethral sphincter (28) in approximate alignment with pubic bone (26). Urethral sphincters (28, 30) are muscles that cooperate to moderate the passage of urine from the bladder (24), through the urethra (22), and to external urethral orifice (20). Internal urethral sphincter (28) is made of smooth muscle and thus is under involuntary control. In contrast, external urethral sphincter (30) is made of skeletal muscle and thus is activated by voluntary control.

Urinary incontinence is a condition in which the urethral sphincters (28, 30) of an individual fail to adequately seal the urethra (22), resulting in uncontrolled leaking of urine through the external urethral orifice (20). Stress urinary incontinence is the leaking of urine through the urethra (22) in response to physical stress being exerted on the bladder (24), for example when coughing, sneezing, laughing, exercising, or engaging in other physical activities such as lifting heavy objects. Stress urinary incontinence has been known to be particularly prevalent in women. The exemplary urinary incontinence devices (100, 200) described below are suitably configured to be implanted within female anatomy to augment the female urethral sphincters (28, 30) and thereby treat urinary incontinence, including stress urinary incontinence. In particular, as described below, each device (100, 200) includes a plurality of magnetically biased bodies (102, 104, 202, 204) configured to extend around the anterior side of urethra (22), and a flexible band (106, 208) configured to extend around the posterior side urethra (22) so as to not impinge upon vaginal wall (12). While devices (100, 200) are shown and described in the context of treating urinary incontinence in females, it will be appreciated that devices (100, 200) may be employed in various other medical applications to augment closure of a selected anatomical passageway.

Figure 3:
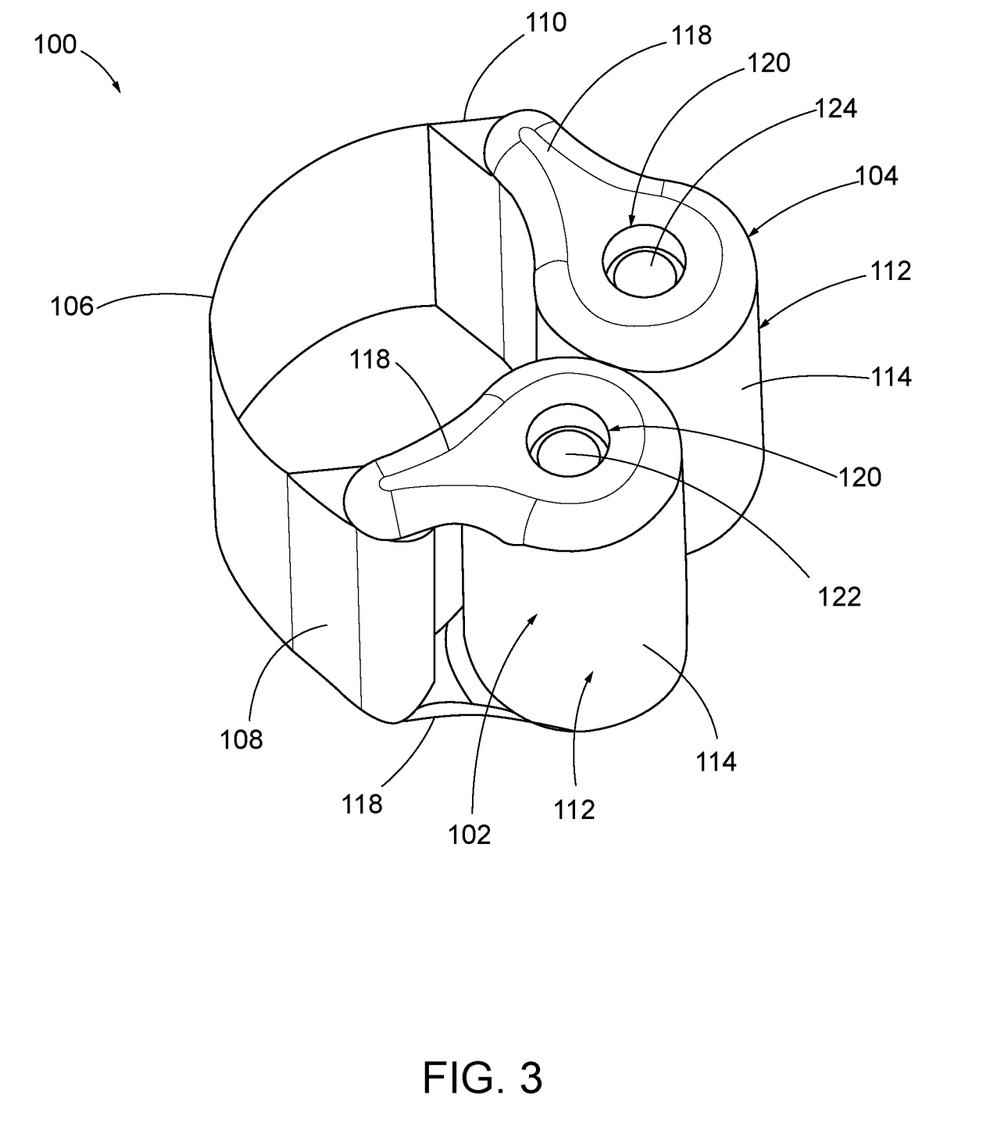
FIG. 3 depicts a perspective of an exemplary sphincter augmentation device.

A. Exemplary Sphincter Augmentation Device Having Magnetic Beads with Elongate Magnets FIG. 3 shows an exemplary sphincter augmentation device (100) configured to treat urinary incontinence in a female patient (P). Device (100) includes a pair of magnetically attracted bodies in the form of a first bead (102) and a second bead (104), and a flexible band (106) having a first end (108) affixed to first bead (102) and a second end (110) affixed to second bead (104). Band (106) is configured to flex to permit device (100) to transition between a radially expanded state and a radially contracted state, described in greater detail below. Flexible band (106) may be formed of any suitably flexible, biocompatible material, such as Gore-Tex or a variety of biocompatible fabrics apparent to those of ordinary skill in the art in view of the teachings herein.

Figure 4:
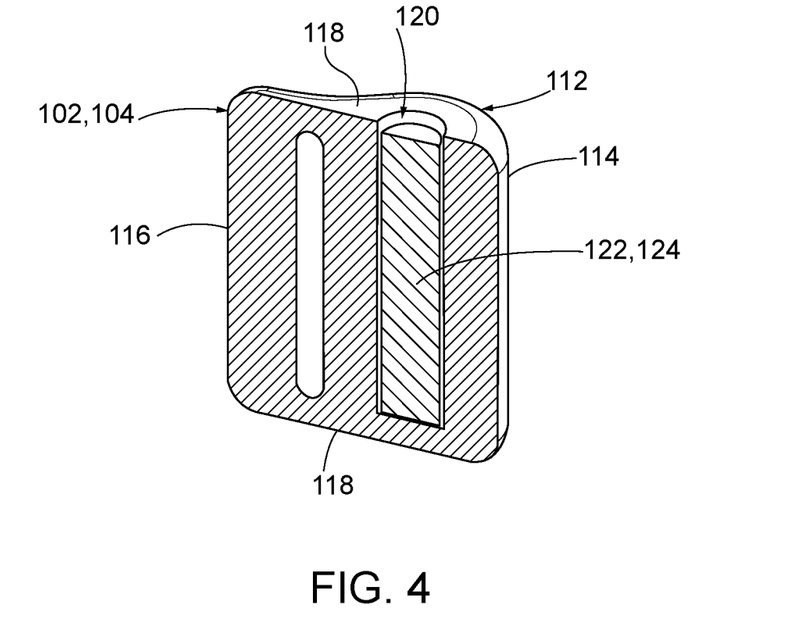
FIG. 4 depicts a cross-sectional side view of a bead of the sphincter augmentation device of FIG. 3.

As shown in FIGS. 3 and 4, first and second beads (102, 104) of the present example are identical in structure and each includes a bead body (112) having a cylindrical portion (114) and an elongate lug (116). Lug (116) is spaced transversely from and is connected to cylindrical portion (114) by a pair of arms (118) that extend transversely from opposed ends of cylindrical portion (114). In the present example, lug (116) extends parallel to cylindrical portion (114) and is formed with a smaller maximum diameter than cylindrical portion (114). Bead body (112) may be formed of any suitable biocompatible material, such as titanium or other biocompatible metals, or a biocompatible plastic.

As shown in FIG. 3, lug (116) of first bead (102) is configured to retain first end (108) of flexible band (106), and lug (116) of second bead (104) is configured to retain second end (110) of flexible band (106). In the present version of sphincter augmentation device (100), each band end (108, 110) is shown looped around the respective lug (116), though it will be appreciated that band ends (108, 110) may be affixed to lugs (116) in various other manners in other examples. It will be further appreciated that band ends (108, 110) may be secured to beads (102, 104) in a variety of other manners using a variety of other suitable structures readily apparent to those of ordinary skill in the art in view of the teachings herein.

Cylindrical portion (114) of each bead body (112) includes a longitudinally extending cavity (120) that houses a respective elongate magnet (122, 124). Each cavity (120) includes a closed first end an open second end through which the respective elongate magnet (122, 124) is configured to be inserted during assembly of device (100). Elongate magnets (122, 124) of the present example are in the form of cylindrical permanent magnets, such as neodymium rare-earth magnets, though elongate magnets (122, 124) may be of various other elongate shapes and permanent magnet materials in other examples. As described below in connection with FIGS. 5 and 6, elongate magnets (122, 124) have inverse magnetization patterns that results in beads (102, 104) being magnetically biased toward one another along their respective longitudinal axes. The elongate shape of magnets (122, 124) maximizes the surface area over which their magnetic attraction forces are exerted, thus maximizing the pressure that can be retained by sphincter augmentation device (100) during use.

Figure 5:
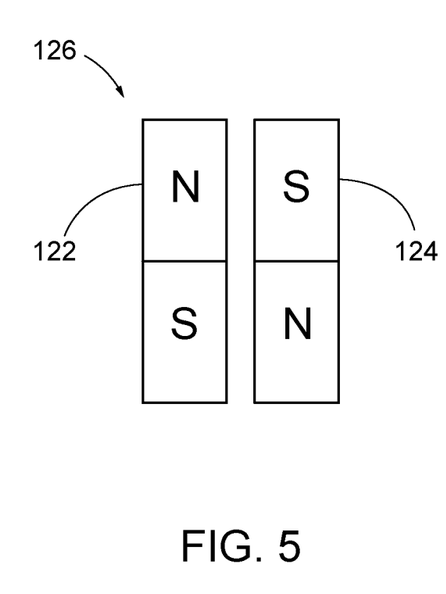
FIG. 5 depicts a schematic side view of first and second magnets of the sphincter augmentation device of FIG. 3, showing a first exemplary magnetization pattern of the magnets.

FIG. 5 shows a first exemplary magnetization configuration (126) of elongate magnets (122, 124) in which the polarity of each elongate magnet (122, 124) varies along its length, across a traverse plane extending through elongate magnet (122, 124). Elongate magnets (122, 124) are positioned within their respective bead body cavities (120) in reverse orientations such that the upper half and the lower half of first magnet (122) differs in polarity from the upper half and the lower half of the second magnet (124), such that beads (102, 104) are magnetically attracted to one another along their longitudinal axes.

Figure 6:
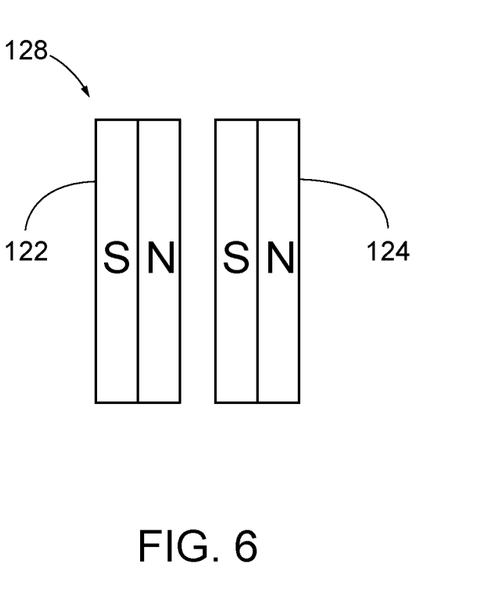
FIG. 6 depicts a schematic side view of the first and second magnets of the sphincter augmentation device of FIG. 3, showing a second exemplary magnetization pattern of the magnets.

FIG. 6 shows a second exemplary magnetization configuration (128) in which the polarity of each elongate magnet (122, 124) varies along its width, across a longitudinal plane extending through elongate magnet (122, 124). Elongate magnets (122, 124) are positioned within their respective bead cavities (120) in the same orientation such that confronting sides of magnets (122, 124) are of opposing polarities, resulting in beads (102, 104) being magnetically attracted to one another along their longitudinal axes.

Figure 7:
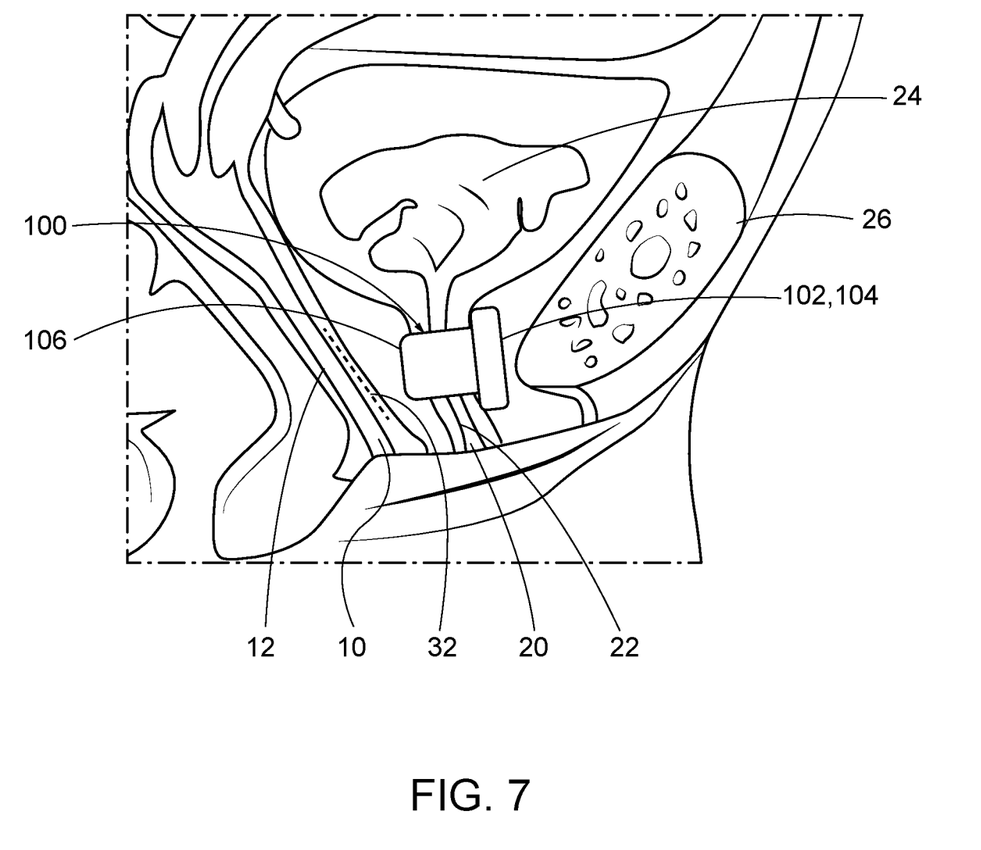
FIG. 7 depicts an enlarged cross-sectional side view of a female patient, taken along the sagittal plane, showing the sphincter augmentation device of FIG. 3 being implanted through a vaginal wall and positioned about the urethra.

As shown in FIGS. 3 and 7, beads (102, 104) are configured to magnetically attract one another such that sphincter augmentation device (100) is magnetically biased into a radially contracted state in which beads (102, 104) directly contact one another, or at least approximate and confront one another, to define a substantially annular or closed-loop shape. In a radially contracted state of device (100), beads (102, 104) define a first circumferential portion of device (100) and band (106) defines an opposed second circumferential portion of device (100). Accordingly, device (100) is biased toward a configuration in which beads (102, 104) are arranged non-axisymmetrically about a central axis of device (100).

As shown in FIG. 7, sphincter augmentation device (100) is configured to be implanted within a female patient (P) and positioned circumferentially about urethra (22) to assist urethral sphincters (28, 30) in maintaining urethra (22) in a radially compressed, sealed state until patient (P) makes a voluntary decision to urinate. In the exemplary procedure shown, device (100) is implanted transvaginally through an incision (32) formed in the anterior side of vaginal wall (12), and then positioned circumferentially about urethra (22). Such implantation may include forming a pocket-like space around the portion of the urethra (22) being encircled by device (100), via dissection of surrounding tissue. In other examples, device (100) may be implanted within patient (P) and positioned about urethra (22) using a variety of other surgical methods that will be readily apparent to those of ordinary skill in the art in view of the teachings herein. For example, device (100) may be implanted transcutaneously through an opening formed in a lower abdominal region of patient (P) proximate to the portion of urethra (22) to be encircled by device (100). Such transcutaneous delivery may be performed using a variety of suitable surgical instruments readily apparent to those of ordinary skill in the art, such as endoscopic instruments, for example.

As shown in FIG. 7, sphincter augmentation device (100) is positioned about urethra (22) such that beads (102, 104) are disposed on an anterior side of urethra (22) and flexible band (106) extends about a posterior side of urethra (22). Such positioning of device (100) relative to urethra (22) ensures that device (100) does not impinge upon adjacent anatomical structures, including the anterior side of vaginal wall (12). In that regard, as shown best in FIG. 3, flexible band (106) is formed with a maximum thickness in a radial direction of device (100) that is significantly less than a maximum thickness of each bead (102, 104) in a radial direction of device (100). Accordingly, flexible band (106) occupies a much smaller volume of space in a radial direction of device (100) than beads (102, 104), such that band (106) may be positioned in the small space between the posterior side of urethra (22) and the anterior side of vaginal wall (12) without impinging on vaginal wall (12). Moreover, flexible band (106) is formed with a width in an axial direction of device (100) that is suitable to disperse the constrictive pressure exerted by band (106) on the encircled portion of urethra (22), thereby avoiding damage to urethra (22), while still applying sufficient pressure on urethra (22) to effectively augment urethral sphincters (28, 30), as described below.

In use, sphincter augmentation device (100) is configured to apply a degree of circumferential constriction to urethra (22) that effectively augments urethral sphincters (28, 30) to prevent unwanted leakage of urine through urethra (22), while still permitting expansion of urethra (22) for voluntary urination. This functionality is provided by the magnetic attraction of beads (102, 104), which biases device (100) toward a radially contracted state in which band (106) and beads (102, 104) bear radially inwardly against the surrounded portion of urethra (22) and thereby cinch the surrounded portion closed to prevent urine leakage through urethra (22). Bead magnets (122, 124) are suitably configured to exert a mutual magnetic attraction force on one another that is high enough to maintain urethra (22) in a constricted state to prevent unwanted leakage of urine, but also low enough to permit separation of beads (102, 104) and expansion of urethra (22) in response to urine being forced through the encircled portion of urethra (22) when patient (P) activates voluntary muscles for intentional urination. By way of example only, bead magnets (122, 124) may be configured to separate in response to a separation force of approximately 15 grams-force. In some instances, the elongate shape of beads (102, 104) and magnets (122, 124) may result in the longitudinal ends of beads (102, 104) prying apart from one asynchronously so as to define a V-like shape.

Figure 8:
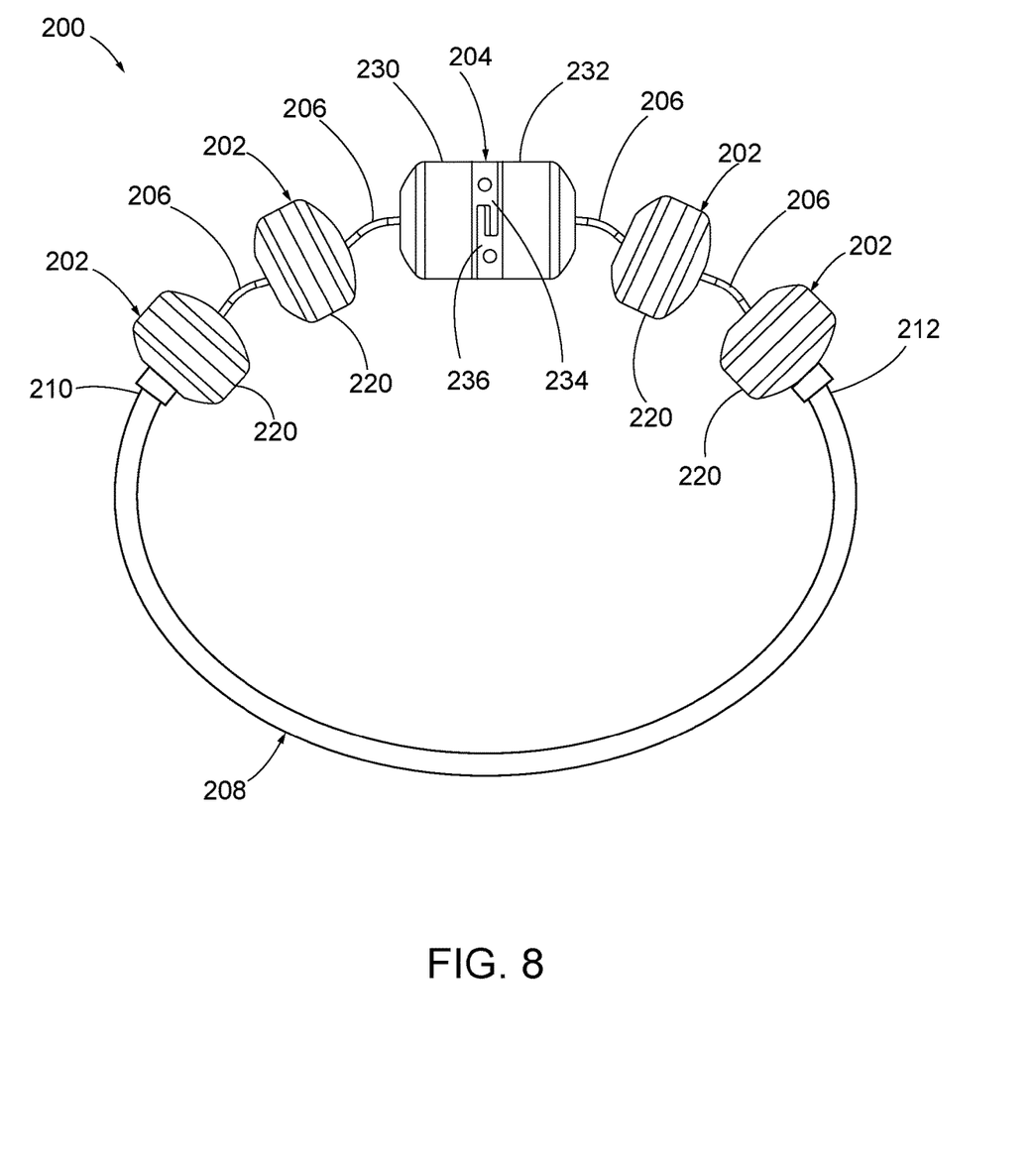
FIG. 8 depicts a top plan view of another exemplary sphincter augmentation device.
Figure 9:
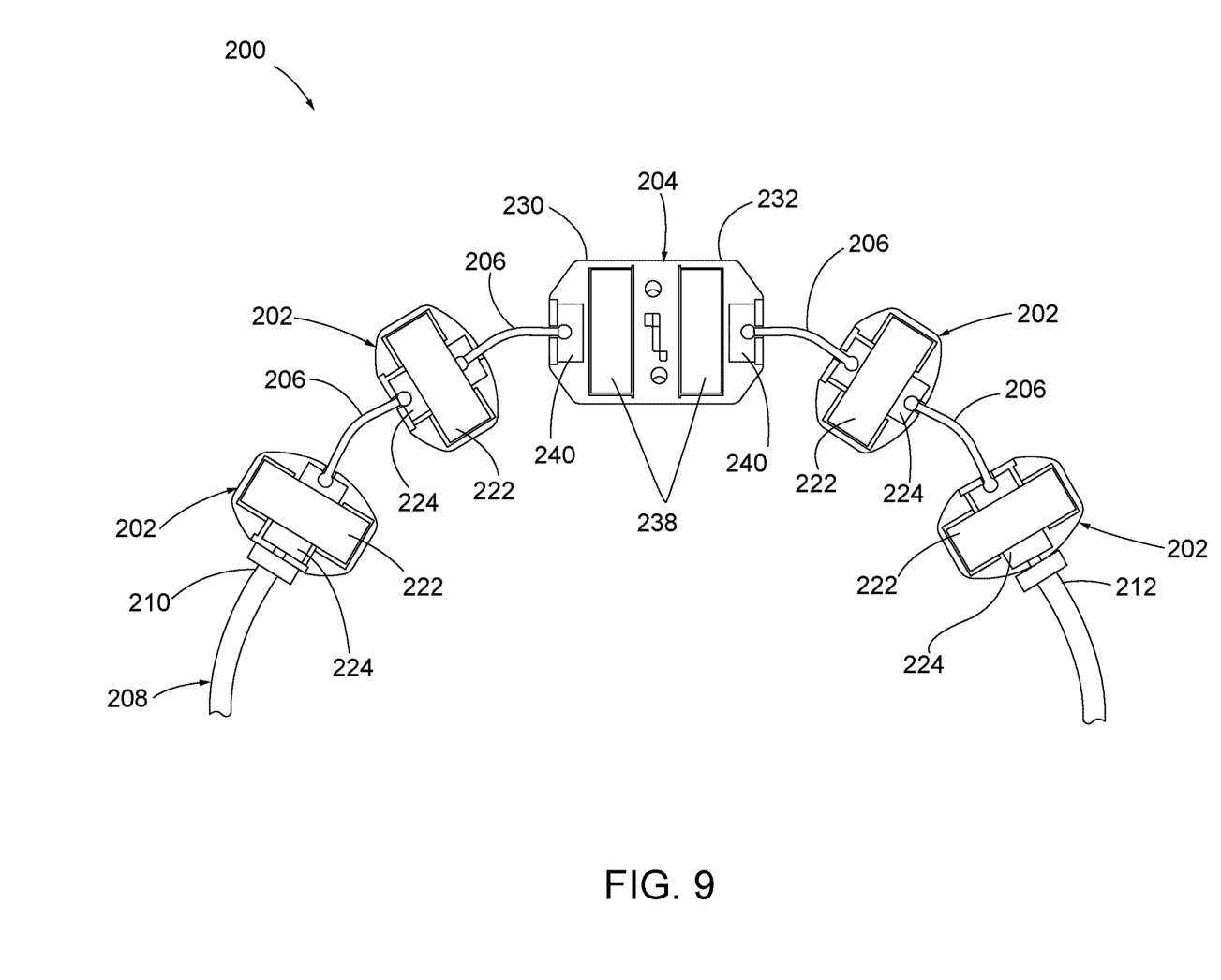
FIG. 9 depicts an enlarged top plan view of the sphincter augmentation device of FIG. 8, with portions of beads thereof omitted to show internal features of the beads.

B. Exemplary Sphincter Augmentation Device Having Magnetic Beads Interconnected with Links FIGS. 8 and 9 show another exemplary sphincter augmentation device (200) configured to treat urinary incontinence in a female patient (P). Device (200) is similar to device (100) described above, except as otherwise described below. Device (200) includes a plurality of magnetically attracted bodies in the form of four side beads (202) and a medial bead (204) arranged between each adjacent pair of side beads (202). Device (200) may include alternative quantities of side beads (202) in other examples. Beads (202, 204) are movably interconnected by a plurality of links (206), each of which is slidably retained by a respective pair of adjacent beads (202, 204). Device (200) further includes a flexible band (208) having a first end (210) affixed to a first terminal side bead (202), and an opposed second end (212) affixed to a second terminal side bead (202).

Like flexible band (106) described above, flexible band (208) is configured to flex to permit sphincter augmentation device (200) to transition between a radially expanded state shown in FIG. 8 and a radially contracted state shown in FIG. 10B, described in greater detail below. Additionally, flexible band (208) is formed with a maximum thickness in a radial direction of device (200) that is significantly less than a maximum thickness of each bead (202, 204) in a radial direction of device (200). Accordingly, similar to flexible band (106), flexible band (208) is advantageously configured to be positioned in the small space between the posterior side of urethra (22) and the anterior side of vaginal wall (12) of patient (P) without impinging on vaginal wall (12). Flexible band (208) may be formed of any suitably flexible, biocompatible material, such as Gore-Tex or a variety of biocompatible fabrics apparent to those of ordinary skill in the art in view of the teachings herein.

As shown best in FIG. 9, each side bead (202) of the present example includes a housing (220), which may comprise two or more coupled parts and may be formed from a non-ferrous material such as titanium or plastic, for example. Each housing (220) houses an annular permanent magnet (222), which may be in the form of a neodymium rare-earth magnet, for example, and which is oriented within the respective side bead (202) such that a central axis of annular magnet (222) extends tangentially relative to a central axis of sphincter augmentation device (200). Each side bead (202) further includes a cylindrical chamber (224) that extends through annular magnet (222), through the respective annular magnet (222), and opens through opposed sides of housing (220). Each cylindrical chamber (224) is configured to slidably receive end portions of a respective pair of links (206), while retaining tips of the links (106) therein.

Medial bead (204) of the present example includes a first medial bead part (230) and a second medial bead part (232) configured to releasably join together to provide sphincter augmentation device (200) with a substantially annular, closed-loop shape. As shown best shown in FIG. 10A, first medial bead part (230) includes a first clasp feature (234) configured to confront and lockingly engage a second clasp feature (236) of second medial bead part (232). Each clasp feature (234, 236) of the present example includes a projection and a corresponding recess configured to mate with the projection and recess of the opposing clasp feature (234, 236). In other examples, clasp features (234, 236) may be substituted with various other suitable types of joining features readily apparent to those of ordinary skill in the art in view of the teachings herein. Each medial bead part (230, 232) also houses an annular permanent magnet (238), which may be similar to annular magnets (222) of side beads (202). Each medial bead part (230, 232) further includes a cylindrical chamber (240) that extends through annular magnet (238) and is configured to slidably receive the end portion of a respective link (206), while retaining a tip of the link (206) therein.

As shown in FIGS. 8 and 9, when medial bead parts (230, 232) are coupled together in a closed configuration, beads (202, 204) define a first circumferential portion of device (200) and band (208) defines an opposed second circumferential portion of device (200), such that beads (202, 204) are arranged non-axisymmetrically about a central axis of device (200). Additionally, annular magnets (222, 238) housed within beads (202, 204) are configured to magnetically bias beads (202, 204) toward one another. Accordingly, magnets (222, 238) and slidable links (206) are configured to enable sphincter augmentation device (200) to transition between a radially contracted state, shown in FIG. 10B, and a radially expanded state, shown in FIG. 8. As device (200) transitions between the radially contracted state and the radially expanded state, the end portions of each link (206) slidably extend from and retract within the inner chambers (224,240) of the two adjacent beads (202, 204) between which the link (206) extends, thereby adjusting an effective circumference of device (200).

Like cylindrical magnets (122, 124) described above, annular magnets (222, 238) are provided with a suitable magnetic strength that enables device (200) to radially contract with sufficient pressure to prevent unwanted urine leakage through urethra (22), but also permits separation of beads (202, 204) into a radially expanded state to permit radial expansion of urethra (22) for passage of urine therethrough during intentional urination. By way of example only, each annular magnet (222, 238) may be provided with a magnetic strength that enables beads (202, 204) to separate from one another in response to an applied separation force of approximately 15 to 20 grams-force.

Beads (202, 204) and links (206) of sphincter augmentation device (200) may be further configured and operable in accordance with any one or more of the teachings of U.S. Pat. No. 7,695,427, entitled "Methods and Apparatus for Treating Body Tissue Sphincters and the Like," issued Apr. 13, 2010; U.S. Pat. No. 8,715,157, entitled "Magnetic Gastric Band or the Like, and Related Methods," issued May 6, 2014; U.S. Pub. No. 2011/0098731, entitled "Magnetically Assisted Clasps for Prosthetic Implants, and Related Methods," published Apr. 28, 2011, now abandoned; U.S. application Ser. No. 15/664,665, entitled "Method for Assisting a Sphincter," filed Jul. 31, 2017, issued as U.S. Pat. No. 10,405,865 on Sep. 10, 2019; and/or U.S. application Ser. No. 15/914,381, entitled "Tunable Magnetic Sphincter Augmentation Device," filed Mar. 7, 2018, issued as U.S. Pat. No. 10,945,738 on Mar. 16, 2021, the disclosures of each of these references being incorporated by reference herein.

Figure 10A:
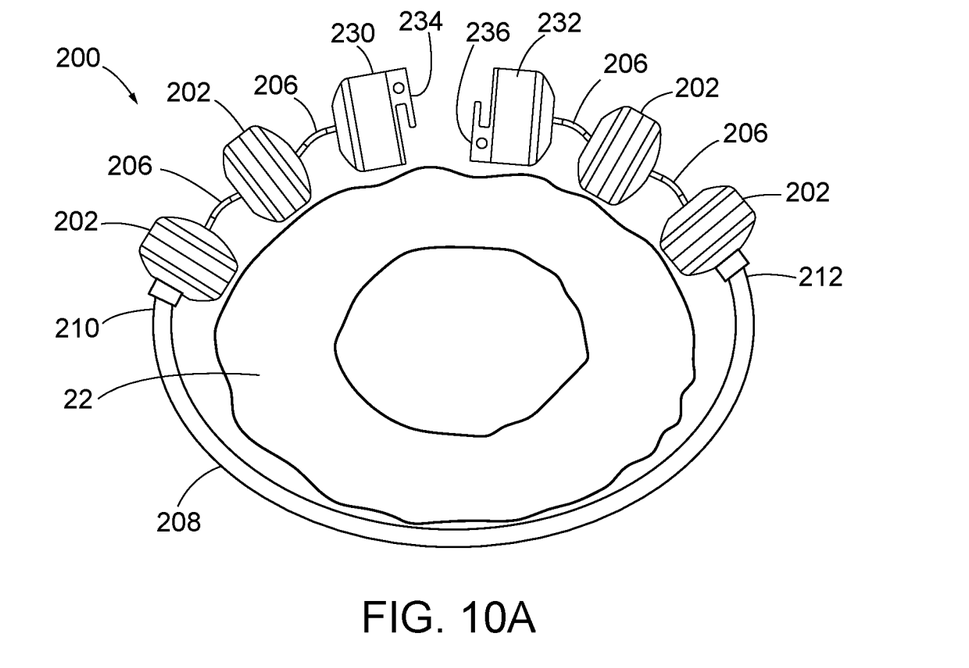
FIG. 10A depicts a schematic top view of the sphincter augmentation device of FIG. 8, showing the device in an unclasped and circumferentially expanded state as the device is being positioned around a urethra.
Figure 10B:
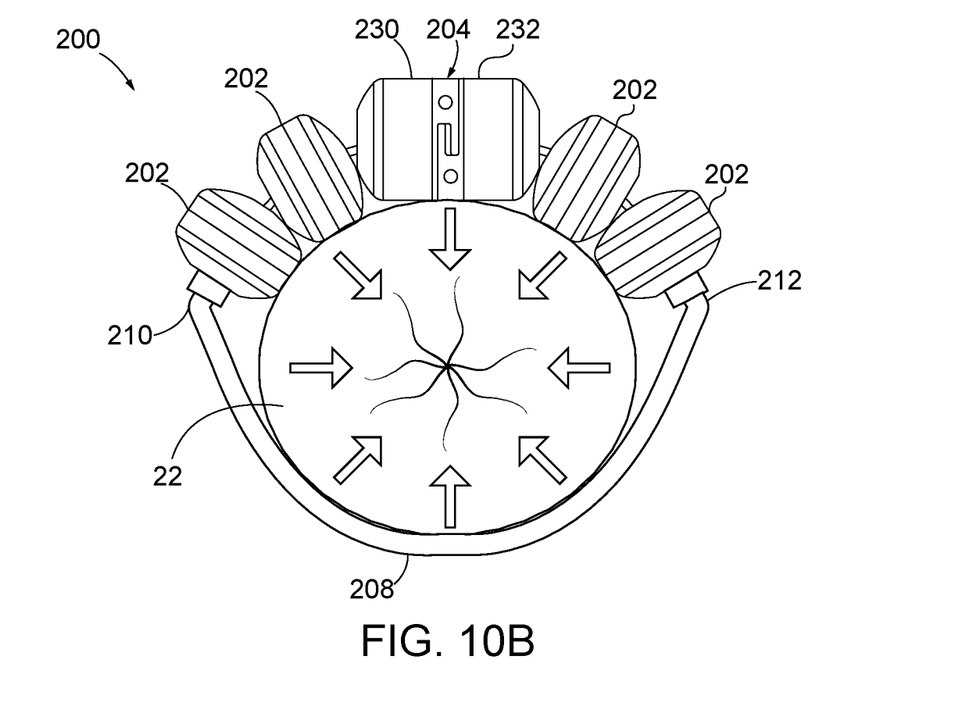
FIG. 10B depicts a schematic top view of the sphincter augmentation device of FIG. 8, showing the device in a clasped and circumferentially contracted state about the urethra.

FIG. 10A shows sphincter augmentation device (200) in an open, expanded state while device (200) is being positioned circumferentially around urethra (22) of female patient (P). Device (200) may be implanted within patient (P) and positioned about urethra (22) using a variety of suitable surgical methods, including those described above in connection with device (100). For instance, device (200) may be implanted transvaginally through an incision (32) formed in the anterior side of vaginal wall (12). Regardless of the method selected for introducing device (200) into patient (P), device (200) is positioned circumferentially about urethra (22) in a manner similar to device (100), such that beads (202) extend about and bear inwardly against an anterior side of the urethra (22) and flexible band (208) extends about and beards inwardly against a posterior side of urethra (22). In that regard, the thin radial thickness of flexible band (208) renders it suitably sized to fit within the small volume of space located between the posterior side of urethra (22) and the anterior side of vaginal wall (32), without impinging upon adjacent anatomical structures such as vaginal wall (32).

Medial bead parts (230, 232) of sphincter augmentation device (200) are joined together via clasp features (234, 236) to secure device (200) about urethra (22). The mutual magnetic attraction of annular magnets (222, 238) biases beads (202, 204) toward one another circumferentially to reduce an effective circumference of device (200) and thereby transition device (200) to a radially contracted state about urethra (22), shown in FIG. 10B. In this radially contracted state, device (200) radially constricts and thereby seals the encircled portion of urethra (22) to prevent unwanted leakage of urine therethrough. Similar to beads (102, 104) of device (100), beads (202, 204) are configured to separate from one another circumferentially and thereby cause device (200) to expand radially in response to an outwardly directed radial force exerted by the encircled portion of urethra (22) as urine is forced therethrough when patient (P) voluntarily activates muscles for intentional urination. When intentional urination is complete, device (200) then reassumes its radially contracted state via the magnetic bias of beads (202, 204), and returns the encircled portion of urethra (22) to a radially constricted, sealed state to prevent unwanted leakage of urine.

II. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A sphincter augmentation device comprising: A sphincter augmentation device comprising: (a) a plurality of bodies defining a first circumferential portion of the device, wherein the bodies are magnetically biased toward one another; and (b) a flexible band coupled with the bodies, wherein the flexible band defines a second circumferential portion of the device such that the bodies are arranged non-axisymmetrically about a central axis of the device, wherein the device is sized to be positioned around a human urethra so that the bodies and the flexible band bear inwardly against the urethra, wherein the device is configured to transition between a radially expanded state and a radially contracted state by the magnetic bias of the bodies to constrict the urethra.

Example 2

The sphincter augmentation device of Example 1, wherein the bodies and the flexible band provide the device with an annular shape in the contracted state.

Example 3

The sphincter augmentation device of any of the preceding Examples, wherein each of the bodies has a first thickness in a radial direction of the device, wherein the flexible band has a second thickness in a radial direction of the device, wherein the second thickness is less than the first thickness.

Example 4

The sphincter augmentation device of any of the preceding Examples, wherein the bodies house a plurality of magnets configured to magnetically bias the bodies toward one another.

Example 5

The sphincter augmentation device of Example 4, wherein at least one of the magnets has a central axis that extends parallel to a central axis of the device.

Example 6

The sphincter augmentation device of any of Examples 4 through 5, wherein at least one of the magnets has a central axis that extends tangentially relative to a central axis of the device.

Example 7

The sphincter augmentation device of any of Examples 4 through 6, wherein at least one of the magnets is cylindrical.

Example 8

The sphincter augmentation device of any of Examples 4 through 7, wherein at least one of the magnets is annular.

Example 9

The sphincter augmentation device of any of the preceding Examples, wherein the plurality of bodies includes a first body and a second body, wherein a first end of the flexible band is coupled to the first body, wherein a second end of the flexible band is coupled to the second body, wherein the first and second bodies are configured to contact one another when the device assumes the contracted state, wherein the first and second bodies are configured to separate from one another when the device assumes the expanded state.

Example 10

The sphincter augmentation device of any of the preceding Examples, further comprising a plurality of links that interconnect the bodies.

Example 11

The sphincter augmentation device of any of the preceding Examples, further comprising a clasp feature arranged between an adjacent pair of the bodies.

Example 12

The sphincter augmentation device of any of the preceding Examples, wherein the bodies comprise a biocompatible metal.

Example 13

The sphincter augmentation device of any of the preceding Examples, wherein the bodies comprise titanium.

Example 14

The sphincter augmentation device of any of the preceding Examples, wherein the flexible band comprises a biocompatible fabric.

Example 15

The sphincter augmentation device of any of the preceding Examples, wherein the flexible band comprises Gore-Tex.

Example 16

A sphincter augmentation device comprising: (a) a first body that houses a first magnet; (b) a second body that houses a second magnet, wherein the first body and the second body are disposed on a first side of the device; and (c) a flexible band coupled with the first body and the second body, wherein at least a portion of the flexible band is disposed on a second side of the device opposed from the first side, wherein the device is sized to be positioned around a human urethra so that the first and second bodies and the flexible band bear inwardly against the urethra, wherein the device is configured to transition from an expanded state to a contracted state by magnetic attraction of the first and second magnets to constrict the urethra.

Example 17

The sphincter augmentation device of Example 16, wherein the first magnet comprises a first cylindrical magnet and the second magnet comprises a second cylindrical magnet.

Example 18

The sphincter augmentation device of any of Examples 16 through 17, further comprising a clasp feature provided on the first side of the device between the first body and the second body.

Example 19

A method of implanting a sphincter augmentation device within a human patient, wherein the device comprises a plurality of bodies magnetically biased toward one another and a flexible band coupled with the bodies, the method comprising: (a) forming an opening in the patient; (b) directing the device through the opening; and (c) positioning the device around a urethra of the patient such that the bodies extend about a first circumferential portion of the urethra and the flexible band extends about an opposed second circumferential portion of the urethra, wherein the magnetic bias of the bodies is configured to reduce an effective circumference of the device about the urethra and thereby constrict the urethra.

Example 20

The method of Example 19, wherein forming an opening in the patient comprises forming an incision in a vaginal sidewall of the patient.

III. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A sphincter augmentation device comprising:
   (a) a plurality of bodies defining a first circumferential portion of the device, wherein the bodies are magnetically biased toward one another;
   (b) a flexible band coupled with the bodies, wherein the flexible band defines a second circumferential portion of the device such that the bodies are arranged non-axisymmetrically about a central axis of the device, wherein the flexible band includes a first end coupled with a first body of the plurality of bodies and a second end coupled with a second body of the plurality of bodies, wherein the flexible band extends continuously from the first end to the second end without any bodies being positioned along the flexible band between the first and second ends; and
   (c) a clasping structure including first and second clasp features disposed within the clasping structure, wherein the first and second clasp features are configured to be joined together, wherein the device is sized to be positioned around a human urethra so that the bodies and the flexible band bear inwardly against the urethra, wherein the device is configured to transition between a radially expanded state and a radially contracted state by the magnetic bias of the bodies to constrict the urethra.

2. The sphincter augmentation device of claim 1, wherein the bodies and the flexible band provide the device with an annular shape in the contracted state.

3. The sphincter augmentation device of claim 1, wherein each of the bodies has a first thickness in a radial direction of the device, wherein the flexible band has a second thickness in a radial direction of the device, wherein the second thickness is less than the first thickness.

4. The sphincter augmentation device of claim 1, wherein the bodies house a plurality of magnets configured to magnetically bias the bodies toward one another.

5. The sphincter augmentation device of claim 4, wherein at least one of the magnets has a central axis that extends parallel to a central axis of the device.

6. The sphincter augmentation device of claim 4, wherein at least one of the magnets has a central axis that extends tangentially relative to a central axis of the device.

7. The sphincter augmentation device of claim 1, further comprising a plurality of links that interconnect the bodies.

8. The sphincter augmentation device of claim 1, wherein the bodies comprise a biocompatible metal.

9. The sphincter augmentation device of claim 1, wherein the flexible band comprises a biocompatible fabric.

10. The sphincter augmentation device of claim 1, wherein the flexible band comprises Gore-Tex.

11. The sphincter augmentation device of claim 1, wherein the clasping structure is magnetically biased towards the plurality of bodies.

12. The sphincter augmentation device of claim 1, wherein the flexible band extends continuously from the first end to the second end without a clasping feature.

13. The sphincter augmentation device of claim 1, wherein the flexible band has a uniform cross-sectional profile extending from the first end to the second end.

14. A sphincter augmentation device comprising:
   (a) a first body including a first post operatively attached to a first cylindrical portion that houses a first magnet;
   (b) a second body including a second post operatively attached to a second cylindrical portion that houses a second magnet, wherein the first body and the second body are disposed on a first side of the device; and
   (c) a flexible band looped around the respective first post of the first body and the second post of the second body, wherein at least a portion of the flexible band is disposed on a second side of the device opposed from the first side, wherein the flexible band includes a first end coupled to the first body and a second end coupled to the second body, wherein the flexible band extends continuously from the first end to the second end, wherein the device is sized to be positioned around a human urethra so that the first and second bodies and the flexible band bear inwardly against the urethra, wherein the device is configured to transition from an expanded state to a contracted state by magnetic attraction of the first and second magnets to constrict the urethra.

15. The sphincter augmentation device of claim 14, wherein the first magnet comprises a first cylindrical magnet and the second magnet comprises a second cylindrical magnet.

16. The sphincter augmentation device of claim 14, wherein the first body further includes a first pair of arms that operatively attach the first post to the first cylindrical portion and the second body further includes a second pair of arms that operatively attach the second post to the second cylindrical portion.

17. The sphincter augmentation device of claim 14, wherein the device includes a central axis, wherein the first and second magnets extend parallel to the central axis.

18. The sphincter augmentation device of claim 17, wherein the first magnet includes an upper half and a lower half separated by a transverse plane relative to the central axis, and the second magnet includes an upper half and a lower half separated by the transverse plane, wherein the upper half of the first magnet and the lower half of the second magnet have a first polarity, and the lower half of the first magnet and the upper half of the second magnet have a second polarity that is opposite the first polarity.

19. The sphincter augmentation device of claim 14, wherein the first and second magnets are configured to directly contact or approximate one another in the contracted state and are configured to be spaced apart in the expanded state, wherein the first and second magnets are configured to exert a mutual magnetic attraction force on one another in both the contracted state and the expanded state.

20. A sphincter augmentation device comprising:
 (a) a first body located on a first side of the device, wherein the first body includes a first magnet;
 (b) a second body located on the first side of the device, wherein the second body includes a second magnet;
 (c) a medial body sized larger than the first and second body, wherein the medial body includes a third magnet and fourth magnet; and
 (d) a flexible band coupled with the first and second bodies, wherein at least a portion of the flexible band is disposed on a second side of the device opposite the first side, wherein the flexible band includes a first end connected to the first body and a second end connected to the second body, wherein the flexible band extends continuously from the first end to the second end without any bodies being positioned along the flexible band between the first and second ends,
wherein the device is sized to be positioned around a human urethra so that the first and second bodies and the flexible band bear inwardly against the urethra,
wherein the device is configured to transition from an expanded state to a contracted state by magnetic attraction of the third magnet with one of the first and second magnets and by magnetic attraction of the fourth magnet with the other of the first and second magnets to constrict the urethra.

* * * * *